United States Patent
Couch

[19]

[11] Patent Number: 6,142,967
[45] Date of Patent: Nov. 7, 2000

[54] HEEL PAIN RELIEF METHOD AND BRACE

[76] Inventor: Brian M. Couch, 5 Glencove Ct., Simpsonville, S.C. 29681

[21] Appl. No.: 09/358,051
[22] Filed: Jul. 21, 1999
[51] Int. Cl.[7] ...................................................... A61F 13/00
[52] U.S. Cl. ............................................................. 602/66
[58] Field of Search ................................ 602/27, 65, 66, 602/63, 60; 128/882, 876; 2/239, 240

[56] References Cited

U.S. PATENT DOCUMENTS

| | | | |
|---|---|---|---|
| 4,409,976 | 10/1983 | Pence | 602/65 |
| 5,554,107 | 9/1996 | Shannahan | 602/66 |
| 5,620,413 | 4/1997 | Olson | 602/65 |
| 5,865,779 | 2/1999 | Gleason | 602/30 |

FOREIGN PATENT DOCUMENTS 114560  8/1984  European Pat. Off. ................. 602/65

OTHER PUBLICATIONS

*Manual Therapy "NAGS", "SNAGS", "MWMS" etc., Third Edition*, Author: Brian R. Mulligan, 1995 p. 118–119.

*Primary Examiner*—Kim M. Lee
*Attorney, Agent, or Firm*—William D. Lee, Jr.; Cort Flint

[57] ABSTRACT

The following heel brace and method to reduce heel pain by securing a strap on the outer side of the ankle and bringing the strap under and up to a securing means on the opposite side of the foot whereby the calcaneus or heel bone is rotated to change the contact point of the heel and ground surface.

13 Claims, 4 Drawing Sheets

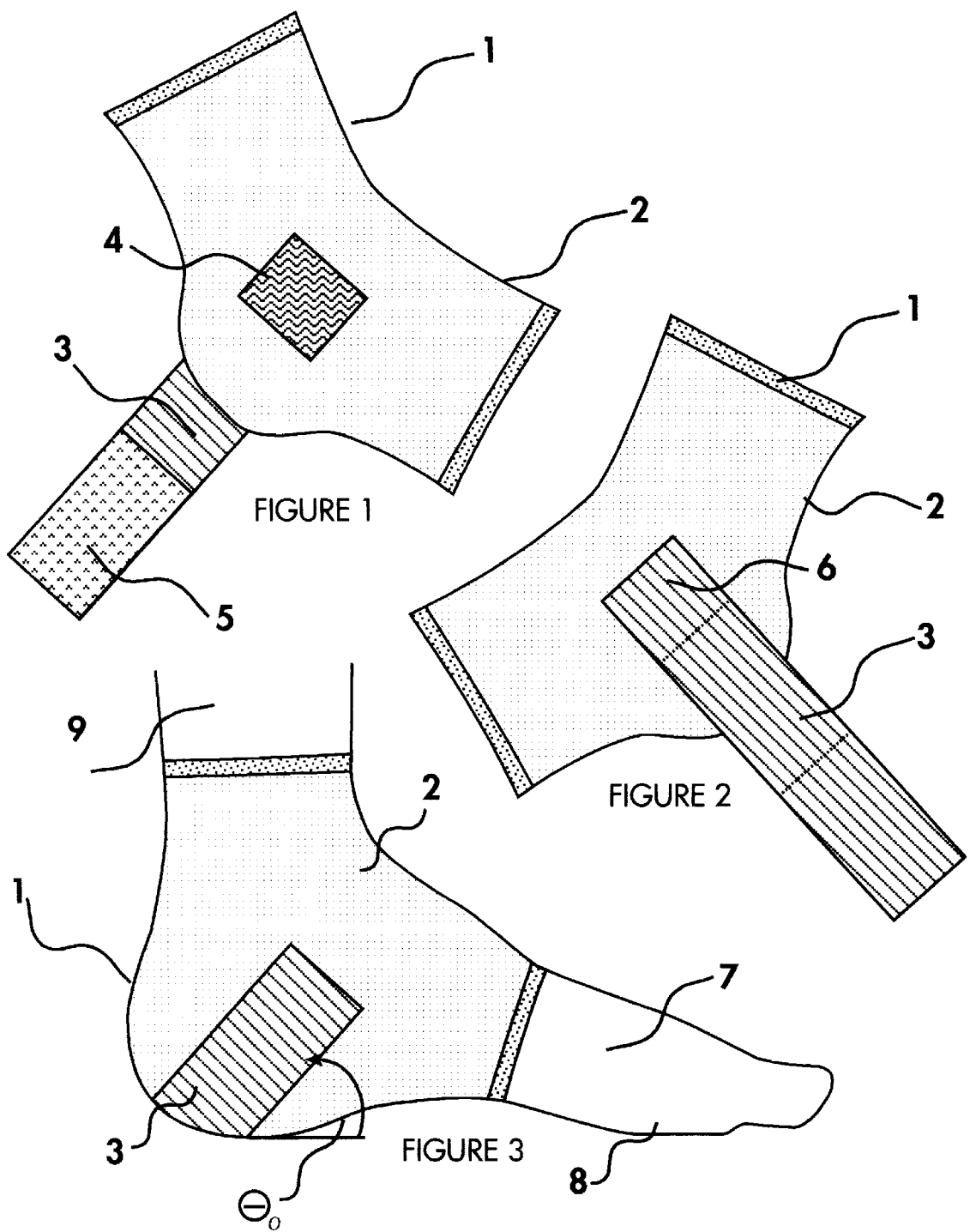

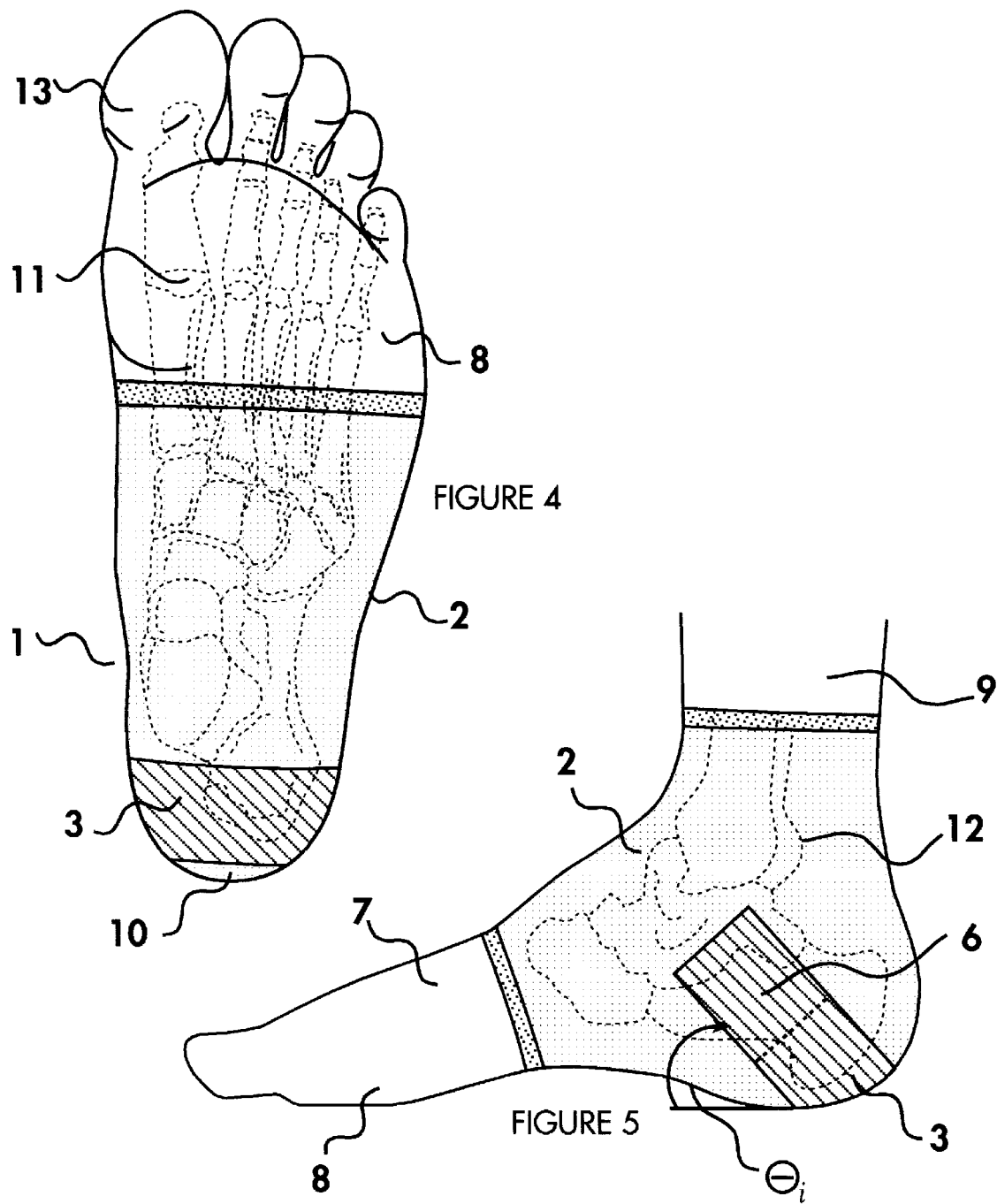

FIGURE 6
FIGURE 7
FIGURE 8
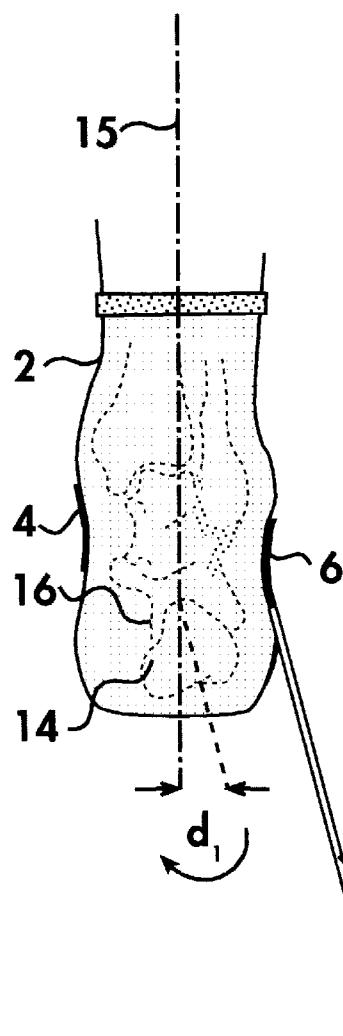
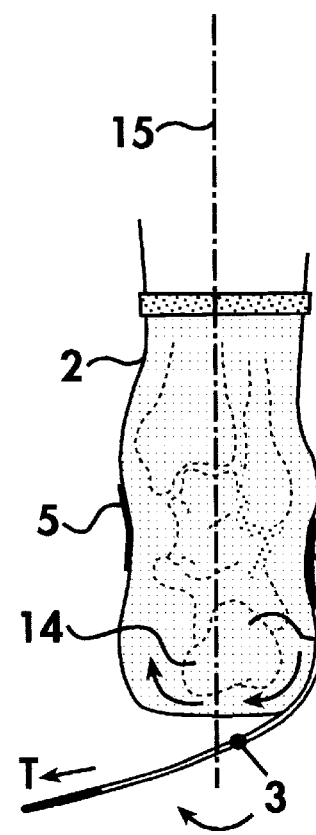
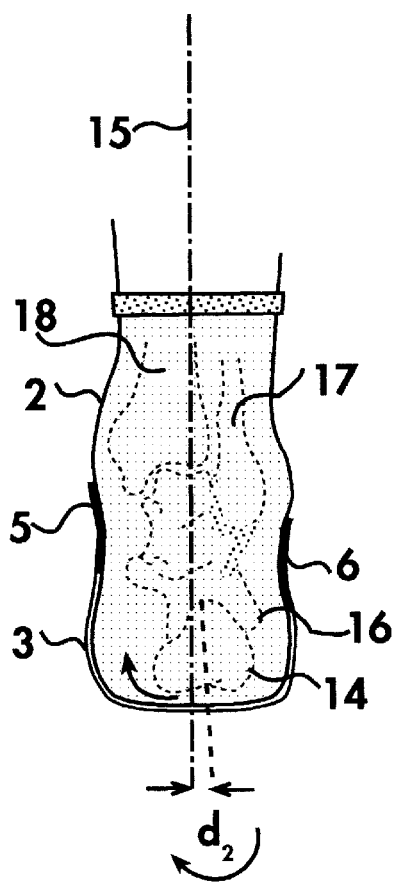

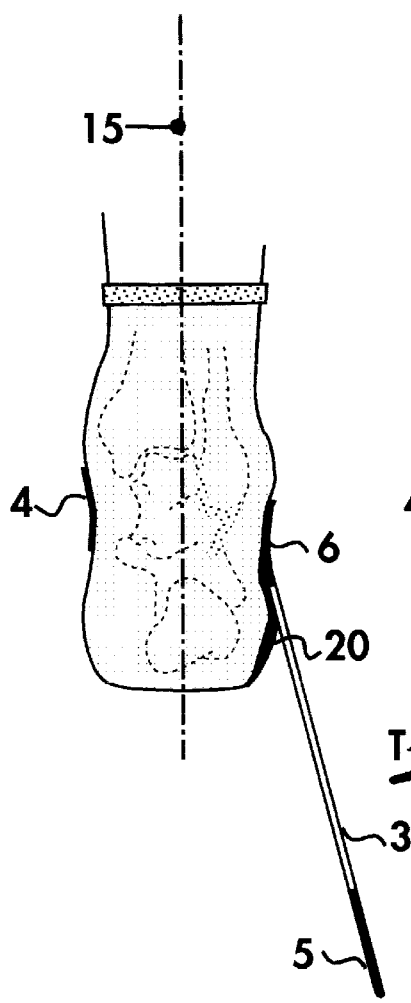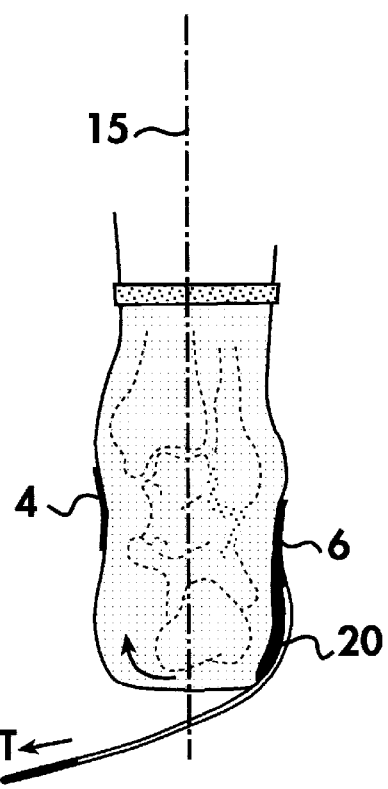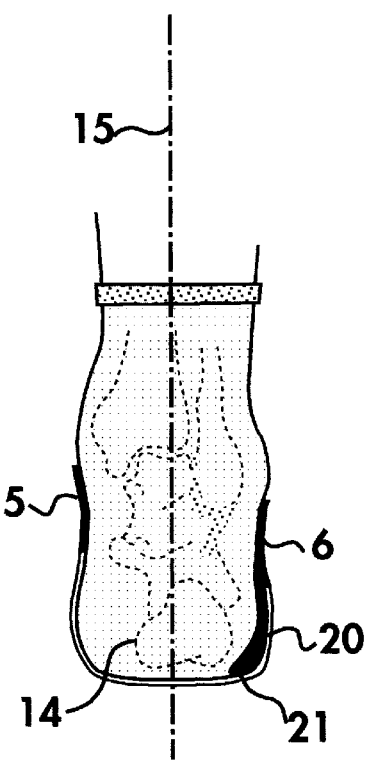

HEEL PAIN RELIEF METHOD AND BRACE

FIELD OF THE INVENTION

This invention relates to a method for relieving heel pain and to a brace for carrying out the method.

BACKGROUND OF THE INVENTION

The occurrence of foot and heel pain is an especially uncomfortable and often debilitating condition which significantly limits activity. It is frequently associated with jogging, tennis, volleyball or other activities which require repeated impact of the tissues on the bottom of the foot and particularly in the heel region. In the anatomy of the human foot, the plantar fascia is the connective tissue on the bottom of the foot which is attached at the front to the metatarsal phalangeal joints, i.e., the metatarsal or toe joints, and at the rear to the calcaneus or heel bone. The plantar fascia acts like a pad to absorb the shock of the forces developed during the strenuous activities mentioned and, during all walking or running activities the plantar fascia stretches and contracts and is subject to impact forces. Continuous stress of the plantar fascia can cause loss of the natural elasticity or padding function of the tissue. This resulting loss of elasticity can produce physical symptoms that include tenderness, swelling, and pain. In some instances bone spurs can develop causing even more pain. To relieve the pain and promote healing, usually requires rest and removal of the cause of the condition which, obviously, is the walking or running.

To treat the condition without surgery it has been a practice to tape a strap to the bottom of the foot to produce an external pull on the plantar fascia and keep the tissue compressed and immobilized, to administer anti-inflammatory drugs to reduce swelling, and to perform stretching exercises for the planar fascia. Often, this treatment is successful but the tape strapping method, to be effective, requires application by trained medical personnel and as the tape loses its adhesion re-taping is required. Accordingly, it is one object of the present invention to provide a method and a brace which can be adjusted readily by the patient.

One elastic brace or foot wrap for treating heel pain is described in U.S. Pat. No. 5,554,107 to Shannahan granted Sep. 10, 1996. This foot wrap comprising an elastic tubular body having an ankle opening, a plurality of toe openings, an arch support, wherein the tubular body exerts a predetermined compressive force to support the arch of the foot. The compressive force is exerted by the wrap along the bottom of the foot from the heel to the toes while additionally providing support for the arch of the foot by means of the arch support. The arch support is drawn around and over the lateral and medial sides of the foot and attached to the top of the tubular body by means of Velcro patches. Among the drawbacks to this foot wrap and method are that it requires enclosing a major portion of the foot inside the foot wrap requiring multiple fittings and adjustments to be properly installed. Accordingly, it is another object of the present invention to provide a wrap or brace which does not need to enclose a large portion of the foot and has a single simple adjustment means.

Another brace is described in U.S. Pat. No. 5,620,413 to Olson granted Apr. 15, 1997 wherein a combination of an ankle brace and wrap is described which is a compressive support sleeve adapted to fit over the foot of a user. A non-elastic strap is secured to a pressure support sleeve and wraps around the plantar fascia of the foot and back around the ankle forming a figure-eight configuration. Two pressure release pads are disposed on a compression support sleeve parallel to each other forming a channel along the Achilles tendon of the patient to provide a redistribution of the forces from the wrap and the Achilles tendon. While this ankle brace adds support to the ankle and to the arch it does not effectively correct any misalignment between the talus and calcaneus which is often the primary source of heel pain. Accordingly, it is still another object of the present invention to correct the alignment between the calcaneus and the ankle joint.

In U.S. Pat. No. 5,865,779 to Gleason granted Feb. 2, 1999 an enveloping elastic sock for treating plantar faciitis is described wherein the sock has a heel opening and exerts compressive force along the longitudinal and transverse axes of a patient's foot. However, the elastic sock described in this patent requires the involvement of the toes with a brace in the back of the heel which is unnecessarily complex and is not directly involved with realigning the calcaneus and ankle joint.

In a prior art strapping method described by Brian Mulligan at page 118 and 119 in his book in an article entitled *Manual Therapy* $3^{rd}$ Edition, Planeview Service, Ltd. Wellington, New Zealand, 1995 describes a method of taping using adhesive to alter the position of the calcaneum in relation to the talus. This is achieved by taping the calcaneum in external rotation. Two strips (approximately two centimeters wide) are used. A first tape is placed obliquely around the back of the heel, and while the calcaneum is forcibly externally rotated and then the tape is wrapped up around the lower leg to maintain the position. The second tape is applied over the first to make the rotation even more effective. When the patients stand they initially have difficulty walking because of the re-positioning but no pain is supposed to be felt. The tape is left for forty-eight hours and the results noted. This part of the treatment for heel pain and may have to be used for a week or two with re-taping. Accordingly, it is still another object of the present invention to provide a method of re-positioning the calcaneus but does not require extensive taping and re-taping of the ankle and foot area and eliminates the discomfort of irritations that may be caused by prolonged adhesive tape contact with the skin.

The foregoing and other objects are achieved by the present invention described below and shown in the attached drawings.

SUMMARY OF THE INVENTION

It has been surprisingly discovered that heel pain can be almost immnediately alleviated by rotating the heel bone or calcaneus with respect to the ankle joint or subtalar joint and maintaining its new position whereby the patient can almost always immediately walk on their re-positioned heel with substantially all of the pain alleviated. This repositioning is achieved and maintained without the use of adhesive tape and minimum patient discomfort is incurred.

In one aspect, the present invention is a heel pain relief method comprising the steps of securing one end of the non-elastic strip to the outside mid-ankle at a position at least the height of the subtalar joint of the ankle; bringing the strap angularly down and rearward under the rear base of the heel so that the strap would form an acute angle with a support surface when standing erect thereupon; applying tension to said strap as it is brought under the heel, and, thereby, re-positioning the calcaneus with respect to the talus by rotating and moving the base of the calcaneus inwardly;

bringing the strap under tension upwardly from the heel base and angularly forward to the inside mid-ankle; and, securing the other end of the tape to the inside of the mid-ankle to retain the tension in the strap and maintain the calcaneus in its re-positioned relationship with the talus thereby relieving heel pain. The method includes providing an elastic sleeve shaped to snugly fit around a human ankle and heel from above the ankle to the mid-arch of the foot; said sleeve having an outside mid-ankle area exterior of said sleeve for securing one end of the strap and having an inside mid-ankle area exterior of the sleeve adapted for attaching the other end of said sleeve securely thereto after the strap has been brought angularly down and around the rear under portion of the heel.

In another aspect, the present invention is a heel pain relief brace comprising a sleeve shaped to snugly fit around a human ankle and heel from above the ankle from the mid-arch of the foot, said sleeve comprising an elastic material that will firmly maintain its dimensional stability when stretched to about its elastic limit; a non-elastic strap affixed at one end thereof to the outside surface of the sleeve and the outer mid-ankle area of the sleeve, said strap being affixed so that it can readily be pulled downwardly and backwardly below the heel; attaching means associated with the other end of said strap when the strap has been pulled under the rear portion of the heel; securing means on the outside surface of the sleeve and the inner mid-ankle area, said securing means being adapted to receive and hold the attaching means and form a firm grip wherein the strap is pulled under the rear portion of the heel to re-position the calcaneus. The securing and attaching means may include Velcro fastener fabric, a buckle, or snaps.

DESCRIPTION OF THE DRAWINGS

The above described invention may be better understood by reference to the drawings which are attached hereto and made part of this specification and illustrate the present invention but are not intended to limit its scope. In the drawings:

FIG. 1 is a representation in elevation of one embodiment of the invention showing the surface from the inner side thereof;

FIG. 2 is a representation in elevation of the heel pain relief brace of the present invention in FIG. 1 showing the surface of the outer side thereof;

FIG. 3 is a representation in elevation showing an ankle and foot positioned in the heel pain relief brace of FIGS. 1 and 2;

FIG. 4 is a view looking at the bottom of the foot shown in FIG. 3 with the bones of the foot and ankle shown in shadow lines;

FIG. 5 is a view of the opposed side of FIG. 3 showing the ankle bones and calcaneus in shadow and also showing the acute angle of the securing strap with the horizontal support of the floor;

FIG. 6 shows the ankle and heel in elevation looking from the rear of the heel with the heel pain relief brace in position prior to the heel adjusting strap being rotated into position;

FIG. 7 is a view of FIG. 6 showing the adjusting strap being rotated into position;

FIG. 8 is a view of FIG. 7 showing the adjusting strap in its secured position; and, FIGS. 9, 10, and 11 are the same views as FIGS. 6, 7, and 8 showing an alternate embodiment of the invention.

DETAILED DESCRIPTION

Turning first to FIG. 1 heel pain relief brace 1 is shown from the outer side and comprises sleeve 2, heel position adjusting strap 3, securing means 4 located at approximately the mid-ankle position, and Velcro mating surface 5 on the strap 3. The sleeve 2 is preferably made from an elastic or suitable fabric such as that which is woven from synthetic yarn sold under brand names such as Spandex or Lycra by duPont. The sleeve 2 can also be formed from neoprene or any similar elastic or rubber-like material which can be perforated to allow the enclosed ankle and foot surface skin to "breathe". Such material when pulled or stretched to near its elastic limit should be secure and dimensionally stable. The Velcro patch 4 is the mating surface for Velcro patch 5 and the Velco surface is made from the mating plastic hooks and loops as sold by Velcro Industries BV of Amsterdam. Other securing means can be a buckle located at position 4 and with a tongue to be inserted in the eyelets on strap 3 so that the strap may be buckled on. A snap fastener arrangement can also be employed. The strap 3 is made from a dimensionally stable, non-elastic material such as woven nylon.

Looking now at FIG. 2, which is the opposite side of brace 1 from that which is shown in FIG. 1, strap 3 is shown secured to strap attachment means 6. The strap attachment may be made with high strength glues which are well known in the art, by sewing, or by rivets or buttons and buttonhole arrangement. That attachment positions 4 and 6 for the strap 3 are in the mid-ankle region which is in the region of the medial malleolus.

FIG. 3 shows the heel pain relief brace 1 from the same or inner side as is shown in FIG. 1 but in FIG. 3 a human foot 7 is inserted into the sleeve 2 which fits the foot in a snug and secure manner. The ball 8 of the foot or pad area extends beyond the sleeve as does the upper ankle or lower leg 9. In FIG. 3 this strap 3 is in place and the angle between the strap and the horizontal surface or floor upon which a foot normally stands is shown. This angle is less than 900 and is preferably in the range of 30° to 60° and most preferably between about 30° to 45°.

FIG. 4 is a view of FIG. 3 from the bottom side of the foot and shows the foot bone structure 11 in shadow line and also illustrates the toes 13. The strap attachment 6 is shown in its preferred position across the heel 10. FIG. 5 shows the opposite side of the foot 7 from that shown in FIG. 3 and this view is from the inner side of the ankle. The inner side is the side which is on the left of the bottom of the foot shown in FIG. 4 and the inner side is the side on which the big toe is located. In FIG. 5 the strap 3 is shown in position and attached at sleeve attachment 6 and the strap 2 makes an angle $\theta_i$. And like the angle on the opposite side as shown in FIG. 3, the angle $\theta_o$ and $\theta_i$ should be approximately the same.

Looking next at FIGS. 6, 7, and 8 the method of the invention will be described. In each of these figures the lower leg, ankle, and foot are shown from the rear and in this arrangement the foot would be the right foot wherein the strap 3 is fastened to the sleeve at attachment 6. The bones of the ankle are shown in shadow and specifically the calcaneus 14 and talus 16 can be seen. The vertical central line 15 is drawn with respect to the position of the calcaneus 14. Normally there is a 3° to 4° angle from the vertical known as the tibia varum angle of the normal leg which is mildly bowed. One feature of the present invention is that it has been discovered that by rotating the calcaneus in the direction of the natural bow of the foot and leg and securing the calcaneus in this position significantly and almost instantaneously relieves leg or foot pain. Patients are surprised at the quick relief obtained.

The method begins with pulling the strap 3 to the left or to the inside (medially) and applying manual tension T in the direction as shown in FIG. 7. This causes the calcaneus 14 to rotate in the direction shown by the arrows. The purpose is to reduce the magnitude of angle $d_1$ and to bring it to a smaller angle $d_2$ as shown in FIG. 8 as the strap 3 is pulled under the heel as is being done in FIG. 7. The strap is then brought up onto the side of the foot and attached at the matching Velcro pad 5 which is located on the outside of the sleeve 2 on its surface on the inner side of the sleeve. Once secured with the calcaneus rotated with respect to the talus 16 and consequently the tibia 18, realignment is achieved which will reduce heel pain. This is due in part to the fact that the pain producing point on the heel which transfers the contact force of walking to the lateral border of the calcaneus has been moved to a new point of contact with the floor or ground. The point of contact and the calcaneus have been turned in the direction of the natural bow of the leg and foot. The actual rotation of the calcaneus is only a few degrees, less than 5°, and usually in the range of 1° to 3°.

Once the strap 3 has been fastened to the securing patch the realignment of the calcaneus will remain. It is important that when this strap is brought down from its attachment point as shown in FIG. 2 it forms an acute angle $\theta_i$ as shown in FIG. 5 so that it will be comfortably and correctly positioned across the bottom of the heel as shown in FIG. 4. This same angle should approximately be maintained as the strap is brought up on the inner side of the ankle as shown in FIG. 3. When the brace 1 is correctly installed in this manner heel pain will be significantly, if not completely, reduced.

In FIGS. 9, 10, and 11 the addition of reinforcing member or side support member 20 is shown. This is another embodiment of the present invention and comprises a semi-rigid insert which conforms to the shape on the side of the lower ankle and stiffens the area of the sleeve 2 between the securing means 6 and the rear part of the heel to enable the strap to be pulled tightly down around and underneath the heel and fastened to the securing means 5. As can be appreciated, the stiffening or reinforcement 20 is positioned so that its lower edge abuts the bottom of the sleeve and resists turning so that the tension in the strap will be maintained.

Many other embodiments, improvements, and alternates will become evident to those skilled in the art upon having read my foregoing specification and therefore my invention is limited only by the scope of the claims set forth below.

What is claimed is:

1. A heel pain relief method comprising the steps of:
   a) securing one end of a non-elastic strap to the outside mid-ankle at a position at least the height of the subtalar joint of the ankle;
   b) bringing the strap angularly down and rearward under the rear base of the heel so that the strap will form an acute angle with a support surface when standing erect thereupon;
   c) applying tension to said strap as it is brought under the heel; and thereby,
   d) repositioning the calcaneus with respect to the talus by rotating and moving the base of the calcaneus inwardly;
   e) bringing said strap upwardly under tension from the heel base and angularly forward toward the inside mid-ankle; and,
   f) securing the other end strap to the inside of the mid-ankle to retain the tension in the strap and maintain the calcaneus in its repositioned relationship with the talus, thereby releasing heel pain.

2. The method of claim 1 including prior to step a) the steps of:
   i) providing an elastic sleeve shaped to snugly fit around a human ankle and heel from above the ankle to the mid-arch of the foot; said sleeve having an outside mid ankle area exterior of said sleeve for securing one end of said strap and having an inside mid-ankle area exterior of said sleeve adapted for attaching the other end of said strap securely thereto; and after performing step a) of claim 1,
   ii) inserting the foot with the heel needing pain relief into the sleeve so that the sleeve fits snugly about the ankle.

3. The method of claim 2 including prior to performing step b), the steps of:
   i) attaching one Velcro fastener patch to the exterior inside mid-ankle area of said sleeve;
   ii) attaching the other Velcro fastener patch to said other end of said strap whereby said strap may be secured when performing step f) of claim 1.

4. The method of claim 1 wherein in step e) the strap is brought over the top of the foot and in step f) the other end of the strap is secured on the outside of the ankle.

5. A heel pain relief brace comprising:
   a) a sleeve shaped to snugly fit around a human ankle and heel from above the ankle to the mid-arch of the foot, said sleeve comprising an elastic material that will firmly maintain its dimensional stability when stretched to about its elastic limit;
   b) a non elastic strap affixed at one end thereof to the outside surface of the sleeve in the outer mid-ankle area of said sleeve, said strap being affixed so that it can readily be pulled downwardly and backwardly below the rear portion of the heel;
   c) attaching means associated with the other end of said strap area, said securing means being adapted to receive and hold the attaching means and form a firm grip when said strap has been pulled under the rear portion of the heel and secured to said securing means to re-position the calcaneus and hold the calcaneous as so repositioned.

6. The brace of claim 5 wherein the securing and attaching means of said strap is a Velcro fastener fabric, one having the fabric with hooks and the other with loops.

7. The brace of claim 5 wherein the attaching means is a series of eyelets in the other end of said strap and the securing means is a buckle and tongue for locking insertion into an eyelet to secure said other end of the strap.

8. The brace of claim 5 wherein said sleeve of said brace is formed of neoprene.

9. The brace of claim 5 wherein said sleeve is formed from woven elastic fabric material.

10. The brace of claim 5 wherein the strap is formed of woven nylon.

11. The brace of claim 5 wherein the securing means is located on the outside mid-ankle surface of the sleeve on the inner side of the ankle and the said one end of said strap is attached below the tibia in a position so that when the calcaneus is rotated 1 degree to 3 degrees from its previous position said strap will hold the calcaneus as repositioned.

12. The brace of claim 5 including an outer side reinforcement member associated with the sleeve for stabilizing the position of said strap.

13. A heel pain relief brace comprising;
   a) a sleeve adapted for snugly fitting around a human ankle with dimensional stability, said sleeve having securing means on its inner ankle side;
   b) a non elastic strap for rotating the calcaneous inwardly to reposition and hold the calcaneous in its new position, said strap being attached to the outer ankle side of said sleeve whereby when pulled downwardly and backwardly under the heel and upwardly to attach to said securing means, said sleeve will cooperate with said strap to maintain the calcaneous in its new position.

* * * * *